(12) United States Patent
Heintzberger et al.

(10) Patent No.: US 9,521,825 B2
(45) Date of Patent: *Dec. 20, 2016

(54) LETTUCE CULTIVAR MONTERRA

(71) Applicant: VANGUARD SEED, INC., Salinas, CA (US)

(72) Inventors: Victor Carl Heintzberger, Salinas, CA (US); John Carl Heintzberger, Salinas, CA (US)

(73) Assignee: VANGUARD SEED, INC., Salinas, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/155,889

(22) Filed: May 16, 2016

(65) Prior Publication Data

US 2016/0338308 A1     Nov. 24, 2016

Related U.S. Application Data

(60) Provisional application No. 62/164,068, filed on May 20, 2015.

(51) Int. Cl.
*A01H 5/12*     (2006.01)

(52) U.S. Cl.
CPC ....................................... *A01H 5/12* (2013.01)

(58) Field of Classification Search
None
See application file for complete search history.

(56) References Cited

U.S. PATENT DOCUMENTS

| | | | |
|---|---|---|---|
| 5,304,719 | A | 4/1994 | Segebart |
| 5,367,109 | A | 11/1994 | Segebart |
| 5,523,520 | A | 6/1996 | Hunsperger et al. |
| 5,763,755 | A | 6/1998 | Carlone |
| 5,850,009 | A | 12/1998 | Kevern |
| 9,380,757 | B2 * | 7/2016 | Heintzberger ........... A01H 5/12 |
| 9,398,753 | B2 | 7/2016 | Heintzberger et al. |
| 2014/0259210 | A1 * | 9/2014 | Heintzberger ........... A01H 5/12 800/274 |

OTHER PUBLICATIONS

Bassett, M.J., "The role of leaf shape in the inheritance of heading in lettuce (*Lactuca sativa* L.)", *J. Am. Soc. Hortic. Sci.*, 1975, 100(2):104-105.

Bennetzen, J.L. and Jones, J.D.G., edited by Setlow, J.K., "Approaches and progress in the molecular cloning of plant disease resistance genes", *Genetic Engineering*, 1992, 14:99-124.

DeBolle, M.F.C., et al., "Antimicrobial peptides from *Mirabilis jalapa* and *Amaranthus caudatus*: expression, processing, localization and biological activity in transgenic tobacco", *Plant Molecular Biology*, 1996, 31:993-1008.

DeVries, I.M. and van Raamsdonk, L.W.D., "Numerical morphological analysis of lettuce cultivars and species (*Lactuca* sect. *Lactuca, Asteracea*)", *Plant Systematics and Evolution*, 1994, 193:125-141.

Eshed, Y. and Zamir, D., "Less-than-additive epistatic interactions of quantitative trait loci in tomato", *Genetics*, 1996, 143:1807-1817.

Kraft, T., Hansen, M., and Nilsson, N.O., "Linkage disequilibrium and fingerprinting in sugar beet", *Theor. Appl. Genet.*, 2000, 101:323-326.

Michelmore, R., et al., "Transformation of lettuce (*Lactuca sativa*) mediated by *Agrobacterium tumefaciens*", *Plant Cell Reports*, 1987, 6:439-442.

Pang, S., et al., "Expression of a gene encoding a scorpion insectotoxin peptide in yeast, bacteria and plants", *Gene*, 1992, 116:165-172.

Ryder, E.J., "Lettuce genetics: Inheritance, linkage and epistasis", *J. Amer. Soc. Hort. Sci.*, 1992, 117(3):504-507.

Ryder, E.J., Kim, Z.H. and Waycott, W., "Inheritance and epistasis studies of chlorophyll deficiency in lettuce", *J. Amer. Soc. Hort. Sci.*, 1999, 124(6):636-640.

Whitaker, T.W., Ryder, E.J. and Hills, O.A., "Lettuce production in the United States, Agriculture Handbook No. 221", Agricultural Research Service of the U.S.D.A., 1974, pp. 4-5.

Waycott, W. and Fort, S.B., "Differentiation of nearly identical germplasm accessions by a combination of molecular and morphologic analyses", *Genome*, 1994, 37(4):577-583.

Xinrun, Z. and Conner, A.J., "Genotypic effects on tissue culture response of lettuce cotyledons", *J. Genet. & Breed.*, 1992, 46:287-290.

U.S. Plant Variety Protection certificate, Kodiak, 200900050, Issued Sep. 14, 2012, 29 pages.

U.S. Plant Variety Protection certificate, Bergam's Green, 200500262, Issued Feb. 5, 2008, 54 pages.

* cited by examiner

*Primary Examiner* — Ashley K Buran

(74) *Attorney, Agent, or Firm* — Jondle & Associates, P.C.

(57) ABSTRACT

A lettuce cultivar, designated Monterra, is disclosed. The invention relates to the seeds, plants and plant parts of lettuce cultivar Monterra and to methods for producing a lettuce plant by crossing the cultivar Monterra with itself or another lettuce cultivar. The invention further relates to methods for producing a lettuce plant containing in its genetic material one or more transgenes and to the transgenic lettuce plants and plant parts produced by those methods. This invention also relates to lettuce cultivars or breeding cultivars and plant parts derived from lettuce cultivar Monterra, to methods for producing other lettuce cultivars, lines or plant parts derived from lettuce cultivar Monterra and to the lettuce plants, varieties, and their parts derived from the use of those methods. The invention further relates to hybrid lettuce seeds, plants, and plant parts produced by crossing cultivar Monterra with another lettuce cultivar.

23 Claims, No Drawings

LETTUCE CULTIVAR MONTERRA

CROSS REFERENCE TO RELATED APPLICATIONS

This application claims the benefit of priority from U.S. provisional patent application Ser. No. 62/164,068 filed on May 20, 2015, which is incorporated herein by reference in its entirety.

BACKGROUND OF THE INVENTION

The present invention relates to a new green leaf lettuce (*Lactuca sativa* L.) variety designated Monterra, which exhibits resistance to lettuce necrotic stunt virus (LNSV) and tan seed color. All publications cited in this application are herein incorporated by reference.

There are numerous steps in the development of any novel, desirable plant germplasm. Plant breeding begins with the analysis and definition of problems and weaknesses of the current germplasm, the establishment of program goals, and the definition of specific breeding objectives. The next step is selection of germplasm that possess the traits to meet the program goals. The goal is to combine in a single variety or hybrid an improved combination of desirable traits from the parental germplasm. These important traits may include increased head size and weight, higher seed yield, improved color, resistance to diseases and insects, tolerance to drought and heat, and better agronomic quality.

Practically speaking, all cultivated forms of lettuce belong to the highly polymorphic species *Lactuca sativa* that is grown for its edible head and leaves. As a crop, lettuce is grown commercially wherever environmental conditions permit the production of an economically viable yield. Lettuce is the world's most popular salad. In the United States, the principal growing regions are California and Arizona which produce approximately 329,700 acres out of a total annual acreage of more than 333,300 acres (USDA 2005). Fresh lettuce is available in the United States year-round although the greatest supply is from May through October. For planting purposes, the lettuce season is typically divided into three categories (i.e., early, mid, and late), with the coastal areas planting from January to August, and the desert regions planting from August to December. Fresh lettuce is consumed nearly exclusively as fresh, raw product and occasionally as a cooked vegetable.

*Lactuca sativa* is in the Cichoreae tribe of the Asteraceae (Compositae) family. Lettuce is related to chicory, sunflower, aster, dandelion, artichoke, and chrysanthemum. *L. sativa* is one of about 300 species in the genus *Lactuca*. There are seven different morphological types of lettuce. The crisphead group includes the iceberg and batavian types. Iceberg lettuce has a large, firm head with a crisp texture and a white or creamy yellow interior. The batavian lettuce predates the iceberg type and has a smaller and less firm head. The butterhead group has a small, soft head with an almost oily texture. The romaine, also known as cos lettuce, has elongated upright leaves forming a loose, loaf-shaped head and the outer leaves are usually dark green. Leaf lettuce comes in many varieties, none of which form a head, and include the green leaf and green oak leaf varieties. Latin lettuce looks like a cross between romaine and butterhead. Stem lettuce has long, narrow leaves and thick, edible stems. Oilseed lettuce is a type grown for its large seeds that are pressed to obtain oil. Latin lettuce, stem lettuce, and oilseed lettuce are seldom seen in the United States.

Lettuce in general is an important and valuable vegetable crop. Therefore, it is desirable to develop new varieties of lettuce having novel and exceptional traits, such as resistances to diseases and unique seed color.

The foregoing examples of the related art and limitations related therewith are intended to be illustrative and not exclusive. Other limitations of the related art will become apparent to those of skill in the art upon a reading of the specification.

SUMMARY OF THE INVENTION

The following embodiments and aspects thereof are described in conjunction with systems, tools, and methods which are meant to be exemplary and illustrative, not limiting in scope. In various embodiments, one or more of the above-described problems have been reduced or eliminated, while other embodiments are directed to other improvements.

According to the invention, there is provided a novel lettuce cultivar designated Monterra. This invention thus relates to the seeds of lettuce cultivar Monterra, to the plants of lettuce cultivar Monterra, and to methods for producing a lettuce plant produced by crossing the lettuce cultivar Monterra with itself or another lettuce plant, to methods for producing a lettuce plant containing in its genetic material one or more transgenes, and to the transgenic lettuce plants produced by that method. This invention also relates to methods for producing other lettuce cultivars derived from lettuce cultivar Monterra and to the lettuce cultivar derived by the use of those methods. This invention further relates to hybrid lettuce seeds and plants produced by crossing lettuce cultivar Monterra with another lettuce variety.

In another aspect, the present invention provides regenerable cells for use in tissue culture of lettuce cultivar Monterra. The tissue culture will preferably be capable of regenerating plants having essentially all of the physiological and morphological characteristics of the foregoing lettuce plant, and of regenerating plants having substantially the same genotype as the foregoing lettuce plant. Preferably, the regenerable cells in such tissue cultures will be callus, protoplasts, meristematic cells, cotyledons, hypocotyl, leaves, pollen, embryos, roots, root tips, anthers, pistils, shoots, stems, petiole flowers, and seeds. Still further, the present invention provides lettuce plants regenerated from the tissue cultures of the invention.

Another aspect of the invention is to provide methods for producing other lettuce plants derived from lettuce cultivar Monterra. Lettuce cultivars derived by the use of those methods are also part of the invention.

The invention also relates to methods for producing a lettuce plant containing in its genetic material one or more transgenes and to the transgenic lettuce plant produced by those methods.

In another aspect, the present invention provides for single gene converted plants of Monterra. The single transferred gene may preferably be a dominant or recessive allele. Preferably, the single transferred gene will confer such traits as male sterility, herbicide resistance, insect or pest resistance, modified fatty acid metabolism, modified carbohydrate metabolism, resistance for bacterial, fungal, or viral disease, male fertility, enhanced nutritional quality, and industrial usage. The single gene may be a naturally occurring lettuce gene or a transgene introduced through genetic engineering techniques.

The invention further provides methods for developing lettuce plants in a lettuce plant breeding program using plant breeding techniques including but not limited to recurrent selection, backcrossing, pedigree breeding, restriction fragment length polymorphism enhanced selection, genetic marker enhanced selection, and transformation. Seeds, lettuce plants, and parts thereof, produced by such breeding methods are also part of the invention.

In addition to the exemplary aspects and embodiments described above, further aspects and embodiments will become apparent by reference by study of the following descriptions.

DETAILED DESCRIPTION OF THE INVENTION

In the description and tables which follow, a number of terms are used. In order to provide a clear and consistent understanding of the specification and claims, including the scope to be given such terms, the following definitions are provided:

Allele. The allele is any of one or more alternative forms of a gene, all of which relate to one trait or characteristic. In a diploid cell or organism, the two alleles of a given gene occupy corresponding loci on a pair of homologous chromosomes.

Backcrossing. Backcrossing is a process in which a breeder repeatedly crosses hybrid progeny back to one of the parents, for example, a first generation hybrid $F_1$ with one of the parental genotype of the $F_1$ hybrid.

Big Vein virus. Big vein is a disease of lettuce caused by Lettuce Mirafiori Big Vein Virus which is transmitted by the fungus *Olpidium virulentus*, with vein clearing and leaf shrinkage resulting in plants of poor quality and reduced marketable value.

Bolting. The premature development of a flowering stalk, and subsequent seed, before a plant produces a food crop. Bolting is typically caused by late planting when temperatures are low enough to cause vernalization of the plants.

*Bremia lactucae*. An Oomycete that causes downy mildew in lettuce in cooler growing regions.

Core diameter. The diameter of the lettuce stem at the base of the cut head.

Core length. Length of the internal lettuce stem measured from the base of the cut and trimmed head to the tip of the stem.

Corky root. A disease caused by the bacterium *Rhizomonas suberifaciens*, which causes the entire taproot to become brown, severely cracked, and non-functional.

Cotyledon. One of the first leaves of the embryo of a seed plant; typically one or more in monocotyledons, two in dicotyledons, and two or more in gymnosperms.

Essentially all the physiological and morphological characteristics. A plant having essentially all the physiological and morphological characteristics means a plant having the physiological and morphological characteristics of the recurrent parent, except for the characteristics derived from the converted gene.

First water date. The date the seed first receives adequate moisture to germinate. This can and often does equal the planting date.

Frame diameter. The frame diameter is a measurement of the lettuce plant diameter at its widest point, measured from the outer most wrapper leaf tip to the outer most wrapper leaf tip.

Gene. As used herein, "gene" refers to a segment of nucleic acid. A gene can be introduced into a genome of a species, whether from a different species or from the same species, using transformation or various breeding methods.

Green leaf lettuce. A type of lettuce characterized by having curled or incised leaves forming a loose green rosette that does not develop into a compact head.

Head diameter. Diameter of the cut and trimmed head, sliced vertically, and measured at the widest point perpendicular to the stem.

Head height. Height of the cut and trimmed head, sliced vertically, and measured from the base of the cut stem to the cap leaf.

Head weight. Weight of saleable lettuce head, cut and trimmed to market specifications.

Lettuce Big Vein virus (LBV). Big vein is a disease of lettuce caused by Lettuce Mirafiori Big Vein Virus which is transmitted by the fungus *Olpidium virulentus*, with vein clearing and leaf shrinkage resulting in plants of poor quality and reduced marketable value.

Lettuce Mosaic virus. A disease that can cause a stunted, deformed, or mottled pattern in young lettuce and yellow, twisted, and deformed leaves in older lettuce.

Lettuce necrotic stunt virus (LNSV). A disease of lettuce that can cause severely stunted plants having yellowed outer leaves and brown, necrotic spotting. LNSV is a soil-borne virus from the Tombusvirus family with no known vector.

Market stage. Market stage is the stage when a lettuce plant is ready for commercial lettuce harvest. In the case of an iceberg variety, the head is solid, and has reached an adequate size and weight.

Maturity date. Maturity refers to the stage when the plants are of full size or optimum weight, in marketable form or shape to be of commercial or economic value.

*Nasonovia ribisnigri*. A lettuce aphid that colonizes the innermost leaves of the lettuce plant, contaminating areas that cannot be treated easily with insecticides.

Plant. "Plant" includes plant cells, plant protoplasts, plant cells of tissue culture from which lettuce plants can be regenerated, plant calli, plant clumps and plant cells that are intact in plants, or parts of plants such as pollen, flowers, seeds, leaves, stems and the like.

Quantitative Trait Loci. Quantitative Trait Loci (QTL) refers to genetic loci that control to some degree, numerically representable traits that are usually continuously distributed.

Ratio of head height/diameter. Head height divided by the head diameter is an indication of the head shape; <1 is flattened, 1=round, and >1 is pointed.

Regeneration. Regeneration refers to the development of a plant from tissue culture.

RHS. RHS refers to the Royal Horticultural Society of England which publishes an official botanical color chart quantitatively identifying colors according to a defined numbering system. The chart may be purchased from Royal Horticulture Society Enterprise Ltd., RHS Garden; Wisley, Woking; Surrey GU236QB, UK.

Rogueing. Rogueing is the process in seed production where undesired plants are removed from a variety. The plants are removed since they differ physically from the general desired expressed characteristics of the variety. The differences can be related to size, color, maturity, leaf texture, leaf margins, growth habit, or any other characteristic that distinguishes the plant.

Romaine lettuce. A lettuce variety having elongated upright leaves forming a loose, loaf-shaped head and the outer leaves are usually dark green.

*Sclerotinia sclerotiorum*. A plant pathogenic fungus that can cause a disease called white mold. Also known as cottony rot, watery soft rot, stem rot, drop, crown rot and blossom blight.

Single gene converted. Single gene converted or conversion plant refers to plants which are developed by a plant breeding technique called backcrossing or via genetic engineering wherein essentially all of the desired morphological and physiological characteristics of a line are recovered in addition to the single gene transferred into the line via the backcrossing technique or via genetic engineering.

Tip burn. Means a browning of the edges or tips of lettuce leaves that has an unknown cause, possibly a calcium deficiency.

Tomato Bushy Stunt. A disease which causes stunting of growth, leaf mottling, and deformed or absent fruit.

VSTMA1. Refers to the mutant allele present in Monterra which confers tan seed color. A representative sample of said mutant allele has been deposited under ATCC Accession number PTA-122176.

The following detailed description is of the currently contemplated modes of carrying out the invention. The description is not to be taken in a limiting sense, but is made merely for the purpose of illustrating the general principles of the invention, since the scope of the invention is best defined by the appended claims.

Broadly, the present invention is directed toward green leaf lettuce varieties that exhibit tan seed color conferred by mutant allele VSTMA1 and also have resistance to lettuce necrotic stunt virus (LNSV) infection, including both plants and seeds. Specifically, the green leaf lettuce variety of the present invention, Monterra, exhibits tan seed color and also has resistance to LNSV infection. To date, there are no known commercial green leaf lettuce varieties for the U.S. market having tan seed color and also having resistance to LNSV. The green leaf lettuce variety exemplified in the present invention, Monterra, is thus different from known varieties of green leaf lettuce in having an unexpected and unique combination of traits. Lettuce cultivar Monterra is a green leaf lettuce variety suitable for carton, whole leaf and processing production in the Western United States. Lettuce cultivar Monterra is resistant to LNSV and tip burn and is moderately tolerant to lettuce big vein virus (LBV) and cold weather heading.

The unique trait of tan seed color exhibited by the green leaf lettuce variety of the present invention is conferred by a mutant allele designated VSTMA1. The allele(s) may be single genetic mutation, a single mutation with modifiers, dominant or recessive alleles, or others. The allele(s) conferring the unique traits of the present invention may be linked or isolated. A complementation test, also called a cis-trans test, may be used for determining whether two mutations associated with a specific phenotype represent two different forms of the same gene (alleles) or are variations of two different genes. Based on the genetics of inheritance of seed color, mutant allele VSTMA1 of the present invention is believed to be a single recessive mutation. The tan seed color mutant was surprisingly discovered from a black seeded leaf lettuce variety and did not segregate for seed color upon subsequent selfing; however, when the tan seed color mutant was crossed, seed color segregation was seen in the progeny and the tan seed color has been introgressed into several other new lettuce cultivars. Additional genetic and molecular testing will determine the mutant allele(s) of the present invention.

The cultivar Monterra has shown uniformity and stability for the traits, within the limits of environmental influence for the traits. It has been self-pollinated a sufficient number of generations with careful attention to uniformity of plant type. The line has been increased with continued observation for uniformity. No variant traits have been observed or are expected in cultivar Monterra.

Lettuce cultivar Monterra has the following morphological and physiological characteristics described in Table 1.

TABLE 1

VARIETY DESCRIPTION INFORMATION

Plant:

Type: Green leaf lettuce
Seed:

Color: Tan
Light dormancy: Present
Heat dormancy: Present
Mature Leaves:

Margin: Serrated
Green color (at harvest maturity): RHS 141A
Anthocyanin distribution: N/A
Glossiness: Dull
Thickness: Thick
Trichomes: Absent
Plant (at market stage):

Height: 11.61 in.
Weight: 17.58 oz.
Frame diameter: 14.72 in.
Head size class: Medium
Butt:

Shape: Semi-prostrate
Midrib: Slightly raised
Core:

Core height from base of head to apex: Average 1.81 in.
Bolting:

First water date: Apr. 13, 2013
Number of days from first water date to first flower: 89 days (Jul. 6, 2013)
Class: Slow bolting
Height of mature seed stalk: Average 40 in.
Bolter habit:

Terminal inflorescence: Present
Lateral shoots: Absent
Basal side shoots: Absent
Primary Adaptation Regions:

Spring area: Desert southwest
Summer area: California coast (Salinas Valley, CA)
Autumn area: California coast (Salinas Valley, CA)/Desert southwest
Winter area: Desert southwest
Disease/Pest Resistance:

Lettuce Necrotic Stunt virus (LNSV): Resistant
Lettuce Mosaic virus: Susceptible
Lettuce Big Vein virus (LBV): Moderately tolerant
Downy Mildew (*Bremia lactucae*): Susceptible
Lettuce aphid (*Nasonovia ribisnigri*): Susceptible
Physiological Responses:

Tip burn: Resistant
Cold weather heading: Moderately tolerant

FURTHER EMBODIMENTS OF THE INVENTION

Lettuce in general, and green leaf lettuce in particular, is an important and valuable vegetable crop. Thus, a continuing goal of lettuce plant breeders is to develop stable, high yielding lettuce cultivars that are agronomically sound. To accomplish this goal, the lettuce breeder must select and develop lettuce plants with traits that result in superior cultivars.

Proper testing should detect any major faults and establish the level of superiority or improvement over current cultivars. In addition to showing superior performance, there must be a demand for a new cultivar that is compatible with industry standards or which creates a new market. The introduction of a new cultivar will incur additional costs to the seed producer, the grower, processor and consumer for special advertising and marketing, altered seed and commercial production practices, and new product utilization. The testing preceding release of a new cultivar should take into consideration research and development costs, as well as technical superiority of the final cultivar. For seed-propagated cultivars, it must be feasible to produce seed easily and economically.

Choice of breeding or selection methods depends on the mode of plant reproduction, the heritability of the trait(s) being improved, and the type of cultivar used commercially (e.g., $F_1$ hybrid cultivar, pureline cultivar, etc.). For highly heritable traits, a choice of superior individual plants evaluated at a single location will be effective, whereas for traits with low heritability, selection should be based on mean values obtained from replicated evaluations of families of related plants. Popular selection methods commonly include pedigree selection, modified pedigree selection, mass selection, and recurrent selection.

The complexity of inheritance influences choice of the breeding method. Backcross breeding is used to transfer one or a few favorable genes for a highly heritable trait into a desirable cultivar. This approach has been used extensively for breeding disease-resistant cultivars. Various recurrent selection techniques are used to improve quantitatively inherited traits controlled by numerous genes. The use of recurrent selection in self-pollinating crops depends on the ease of pollination, the frequency of successful hybrids from each pollination, and the number of hybrid offspring from each successful cross.

Each breeding program should include a periodic, objective evaluation of the efficiency of the breeding procedure. Evaluation criteria vary depending on the goal and objectives, but should include gain from selection per year based on comparisons to an appropriate standard, the overall value of the advanced breeding lines, and the number of successful cultivars produced per unit of input (e.g., per year, per dollar expended, etc.).

Promising advanced breeding lines are thoroughly tested and compared to appropriate standards in environments representative of the commercial target area(s) for at least three years. The best lines are candidates for new commercial cultivars. Those still deficient in a few traits are used as parents to produce new populations for further selection.

These processes, which lead to the final step of marketing and distribution, usually take from ten to twenty years from the time the first cross or selection is made. Therefore, development of new cultivars is a time-consuming process that requires precise forward planning, efficient use of resources, and a minimum of changes in direction.

A most difficult task is the identification of individuals that are genetically superior, because for most traits the true genotypic value is masked by other confounding plant traits or environmental factors. One method of identifying a superior plant is to observe its performance relative to other experimental plants and to a widely grown standard cultivar. If a single observation is inconclusive, replicated observations provide a better estimate of its genetic worth.

The goal of lettuce plant breeding is to develop new, unique, and superior lettuce cultivars. The breeder initially selects and crosses two or more parental lines, followed by repeated selfing and selection, producing many new genetic combinations. The breeder can theoretically generate billions of different genetic combinations via crossing, selfing, and mutations. The breeder has no direct control at the cellular level. Therefore, two breeders will never develop the same line, or even very similar lines, having the same lettuce traits.

Each year, the plant breeder selects the germplasm to advance to the next generation. This germplasm is grown under different geographical, climatic, and soil conditions, and further selections are then made during, and at the end of, the growing season. The cultivars that are developed are unpredictable. This unpredictability is because the breeder's selection occurs in unique environments, with no control at the DNA level (using conventional breeding procedures), and with millions of different possible genetic combinations being generated. A breeder of ordinary skill in the art cannot predict the final resulting lines he develops, except possibly in a very gross and general fashion. The same breeder cannot produce the same line twice by using the exact same original parents and the same selection techniques. This unpredictability results in the expenditure of large research monies to develop superior lettuce cultivars.

The development of commercial lettuce cultivars requires the development of lettuce varieties, the crossing of these varieties, and the evaluation of the crosses. Pedigree breeding and recurrent selection breeding methods are used to develop cultivars from breeding populations. Breeding programs combine desirable traits from two or more varieties or various broad-based sources into breeding pools from which cultivars are developed by selfing and selection of desired phenotypes. The new cultivars are crossed with other varieties and the hybrids from these crosses are evaluated to determine which have commercial potential.

Pedigree breeding is used commonly for the improvement of self-pollinating crops or inbred lines of cross-pollinating crops. Two parents which possess favorable, complementary traits are crossed to produce an $F_1$. An $F_2$ population is produced by selfing one or several $F_1$'s or by intercrossing two $F_1$'s (sib mating). Selection of the best individuals is usually begun in the $F_2$ population. Then, beginning in the $F_3$, the best individuals in the best families are selected. Replicated testing of families, or hybrid combinations involving individuals of these families, often follows in the $F_4$ generation to improve the effectiveness of selection for traits with low heritability. At an advanced stage of inbreeding (i.e., $F_6$ and $F_7$), the best lines or mixtures of phenotypically similar lines are tested for potential release as new cultivars.

Mass and recurrent selections can be used to improve populations of either self- or cross-pollinating crops. A genetically variable population of heterozygous individuals is either identified or created by intercrossing several different parents. The best plants are selected based on individual superiority, outstanding progeny, or excellent combining ability. The selected plants are intercrossed to produce a new population in which further cycles of selection are continued.

Backcross breeding has been used to transfer genes for a simply inherited, highly heritable trait into a desirable homozygous cultivar or line that is the recurrent parent. The source of the trait to be transferred is called the donor parent. The resulting plant is expected to have the attributes of the recurrent parent (e.g., cultivar) and the desirable trait transferred from the donor parent. After the initial cross, individuals possessing the phenotype of the donor parent are selected and repeatedly crossed (backcrossed) to the recurrent parent. The resulting plant is expected to have the attributes of the recurrent parent (e.g., cultivar) and the desirable trait transferred from the donor parent.

The single-seed descent procedure in the strict sense refers to planting a segregating population, harvesting a sample of one seed per plant, and using the one-seed sample to plant the next generation. When the population has been advanced from the $F_2$ to the desired level of inbreeding, the plants from which lines are derived will each trace to different $F_2$ individuals. The number of plants in a population declines with each generation due to failure of some seeds to germinate or some plants to produce at least one seed. As a result, not all of the $F_2$ plants originally sampled in the population will be represented by a progeny when generation advance is completed.

In addition to phenotypic observations, the genotype of a plant can also be examined. There are many laboratory-based techniques available for the analysis, comparison and characterization of plant genotype; among these are Isozyme Electrophoresis, Restriction Fragment Length Polymorphisms (RFLPs), Randomly Amplified Polymorphic DNAs (RAPDs), Arbitrarily Primed Polymerase Chain Reaction (AP-PCR), DNA Amplification Fingerprinting (DAF), Sequence Characterized Amplified Regions (SCARs), Amplified Fragment Length polymorphisms (AFLPs), Simple Sequence Repeats (SSRs—which are also referred to as Microsatellites), and Single Nucleotide Polymorphisms (SNPs).

Isozyme Electrophoresis and RFLPs have been widely used to determine genetic composition. Shoemaker and Olsen (Molecular Linkage Map of Soybean (*Glycine max*), pp. 6.131-6.138 in S. J. O'Brien (ed.) *Genetic Maps: Locus Maps of Complex Genomes*, Cold Spring Harbor Laboratory Press, Cold Spring Harbor, N.Y. (1993)) developed a molecular genetic linkage map that consisted of 25 linkage groups with about 365 RFLP, 11 RAPD, three classical markers, and four isozyme loci. See also, Shoemaker, R. C., RFLP Map of Soybean, pp. 299-309, in Phillips, R. L. and Vasil, I. K. (eds.), *DNA-Based Markers in Plants*, Kluwer Academic Press, Dordrecht, the Netherlands (1994).

SSR technology is currently the most efficient and practical marker technology; more marker loci can be routinely used and more alleles per marker locus can be found using SSRs in comparison to RFLPs. For example, Diwan and Cregan described a highly polymorphic microsatellite locus in soybean with as many as 26 alleles. Diwan, N. and Cregan, P. B., *Theor. Appl. Genet.*, 95:22-225 (1997). SNPs may also be used to identify the unique genetic composition of the invention and progeny varieties retaining that unique genetic composition. Various molecular marker techniques may be used in combination to enhance overall resolution.

Molecular markers, which include markers identified through the use of techniques such as Isozyme Electrophoresis, RFLPs, RAPDs, AP-PCR, DAF, SCARs, AFLPs, SSRs, and SNPs, may be used in plant breeding. One use of molecular markers is Quantitative Trait Loci (QTL) mapping. QTL mapping is the use of markers which are known to be closely linked to alleles that have measurable effects on a quantitative trait. Selection in the breeding process is based upon the accumulation of markers linked to the positive effecting alleles and/or the elimination of the markers linked to the negative effecting alleles from the plant's genome.

Molecular markers can also be used during the breeding process for the selection of qualitative traits. For example, markers closely linked to alleles or markers containing sequences within the actual alleles of interest can be used to select plants that contain the alleles of interest during a backcrossing breeding program. The markers can also be used to select toward the genome of the recurrent parent and against the markers of the donor parent. This procedure attempts to minimize the amount of genome from the donor parent that remains in the selected plants. It can also be used to reduce the number of crosses back to the recurrent parent needed in a backcrossing program. The use of molecular markers in the selection process is often called genetic marker enhanced selection or marker-assisted selection. Molecular markers may also be used to identify and exclude certain sources of germplasm as parental varieties or ancestors of a plant by providing a means of tracking genetic profiles through crosses.

Mutation breeding is another method of introducing new traits into lettuce varieties. Mutations that occur spontaneously or are artificially induced can be useful sources of variability for a plant breeder. The goal of artificial mutagenesis is to increase the rate of mutation for a desired characteristic. Mutation rates can be increased by many different means including temperature, long-term seed storage, tissue culture conditions, radiation (such as X-rays, Gamma rays, neutrons, Beta radiation, or ultraviolet radiation), chemical mutagens (such as base analogs like 5-bromo-uracil), antibiotics, alkylating agents (such as sulfur mustards, nitrogen mustards, epoxides, ethyleneamines, sulfates, sulfonates, sulfones, or lactones), azide, hydroxylamine, nitrous acid, or acridines. Once a desired trait is observed through mutagenesis the trait may then be incorporated into existing germplasm by traditional breeding techniques. Details of mutation breeding can be found in *Principles of Cultivar Development* by Fehr, Macmillan Publishing Company (1993).

The production of double haploids can also be used for the development of homozygous varieties in a breeding program. Double haploids are produced by the doubling of a set of chromosomes from a heterozygous plant to produce a completely homozygous individual. For example, see Wan, et al., *Theor. Appl. Genet.*, 77:889-892 (1989).

Descriptions of other breeding methods that are commonly used for different traits and crops can be found in one of several reference books (e.g., *Principles of Plant Breeding*, John Wiley and Son, pp. 115-161 (1960); Allard (1960); Simmonds (1979); Sneep, et al. (1979); Fehr (1987); "Carrots and Related Vegetable *Umbelliferae*," Rubatzky, V. E., et al. (1999).

With the advent of molecular biological techniques that have allowed the isolation and characterization of genes that encode specific protein products, scientists in the field of plant biology developed a strong interest in engineering the genome of plants to contain and express foreign genes, or additional, or modified versions of native, or endogenous, genes (perhaps driven by different promoters) in order to alter the traits of a plant in a specific manner. Any DNA sequences, whether from a different species or from the same species, which are introduced into the genome using transformation or various breeding methods, are referred to herein collectively as "transgenes." Over the last fifteen to twenty years, several methods for producing transgenic plants have been developed, and the present invention, in particular embodiments, also relates to transformed versions of the claimed line.

Nucleic acids or polynucleotides refer to RNA or DNA that is linear or branched, single or double stranded, or a hybrid thereof. The term also encompasses RNA/DNA hybrids. These terms also encompass untranslated sequence located at both the 3' and 5' ends of the coding region of the gene: at least about 1000 nucleotides of sequence upstream from the 5' end of the coding region and at least about 200 nucleotides of sequence downstream from the 3' end of the coding region of the gene. Less common bases, such as inosine, 5-methylcytosine, 6-methyladenine, hypoxanthine, and others can also be used for antisense, dsRNA, and ribozyme pairing. For example, polynucleotides that contain C-5 propyne analogues of uridine and cytidine have been shown to bind RNA with high affinity and to be potent antisense inhibitors of gene expression. Other modifications, such as modification to the phosphodiester backbone, or the 2'-hydroxy in the ribose sugar group of the RNA can also be made. The antisense polynucleotides and ribozymes can consist entirely of ribonucleotides, or can contain mixed ribonucleotides and deoxyribonucleotides. The polynucleotides of the invention may be produced by any means, including genomic preparations, cDNA preparations, in vitro synthesis, RT-PCR, and in vitro or in vivo transcription.

Plant transformation involves the construction of an expression vector that will function in plant cells. Such a vector comprises DNA comprising a gene under control of, or operatively linked to, a regulatory element (for example, a promoter). The expression vector may contain one or more such operably linked gene/regulatory element combinations. The vector(s) may be in the form of a plasmid, and can be used alone or in combination with other plasmids, to provide transformed lettuce plants using transformation methods as described below to incorporate transgenes into the genetic material of the lettuce plant(s).

Expression Vectors for Lettuce Transformation: Marker Genes

Expression vectors include at least one genetic marker, operably linked to a regulatory element (for example, a promoter) that allows transformed cells containing the marker to be either recovered by negative selection, i.e., inhibiting growth of cells that do not contain the selectable marker gene, or by positive selection, i.e., screening for the product encoded by the genetic marker. Many commonly used selectable marker genes for plant transformation are well known in the transformation arts, and include, for example, genes that code for enzymes that metabolically detoxify a selective chemical agent which may be an antibiotic or an herbicide, or genes that encode an altered target which is insensitive to the inhibitor. A few positive selection methods are also known in the art.

One commonly used selectable marker gene for plant transformation is the neomycin phosphotransferase II (nptII) gene, isolated from transposon Tn5, which when placed under the control of plant regulatory signals confers resistance to kanamycin. Fraley, et al., PNAS, 80:4803 (1983). Another commonly used selectable marker gene is the hygromycin phosphotransferase gene which confers resistance to the antibiotic hygromycin. Vanden Elzen, et al., *Plant Mol. Biol.*, 5:299 (1985).

Additional selectable marker genes of bacterial origin that confer resistance to antibiotics include gentamycin acetyl transferase, streptomycin phosphotransferase, aminoglycoside-3'-adenyl transferase, the bleomycin resistance determinant. Hayford, et al., *Plant Physiol.*, 86:1216 (1988); Jones, et al., *Mol. Gen. Genet.*, 210:86 (1987); Svab, et al., *Plant Mol. Biol.*, 14:197 (1990); Hille, et al., *Plant Mol. Biol.*, 7:171 (1986). Other selectable marker genes confer resistance to herbicides such as glyphosate, glufosinate, or bromoxynil. Comai, et al., *Nature*, 317:741-744 (1985); Gordon-Kamm, et al., *Plant Cell*, 2:603-618 (1990); and Stalker, et al., *Science*, 242:419-423 (1988).

Selectable marker genes for plant transformation that are not of bacterial origin include, for example, mouse dihydrofolate reductase, plant 5-enolpyruvylshikimate-3-phosphate synthase, and plant acetolactate synthase. Eichholtz, et al., *Somatic Cell Mol. Genet.*, 13:67 (1987); Shah, et al., *Science*, 233:478 (1986); and Charest, et al., *Plant Cell Rep.*, 8:643 (1990).

Another class of marker genes for plant transformation requires screening of presumptively transformed plant cells rather than direct genetic selection of transformed cells for resistance to a toxic substance such as an antibiotic. These genes are particularly useful to quantify or visualize the spatial pattern of expression of a gene in specific tissues and are frequently referred to as reporter genes because they can be fused to a gene or gene regulatory sequence for the investigation of gene expression. Commonly used genes for screening presumptively transformed cells include a-glucuronidase (GUS), α-galactosidase, luciferase and chloramphenicol, acetyltransferase. Jefferson, R. A., *Plant Mol. Biol.*, 5:387 (1987); Teeri, et al., *EMBO J.*, 8:343 (1989); Koncz, et al., *PNAS*, 84:131 (1987); and DeBlock, et al., *EMBO J.*, 3:1681 (1984).

In vivo methods for visualizing GUS activity that do not require destruction of plant tissues are available. Molecular Probes, Publication 2908, IMAGENE GREEN, pp. 1-4 (1993) and Naleway, et al., *J. Cell Biol.*, 115:151a (1991). However, these in vivo methods for visualizing GUS activity have not proven useful for recovery of transformed cells because of low sensitivity, high fluorescent backgrounds, and limitations associated with the use of luciferase genes as selectable markers.

More recently, a gene encoding Green Fluorescent Protein (GFP) has been utilized as a marker for gene expression in prokaryotic and eukaryotic cells. Chalfie, et al., *Science*, 263:802 (1994). GFP and mutants of GFP may be used as screenable markers.

Expression Vectors for Lettuce Transformation: Promoters

Genes included in expression vectors must be driven by a nucleotide sequence comprising a regulatory element (for example, a promoter). Several types of promoters are now well known in the transformation arts, as are other regulatory elements that can be used alone or in combination with promoters.

As used herein, "promoter" includes reference to a region of DNA upstream from the start of transcription and involved in recognition and binding of RNA polymerase and other proteins to initiate transcription. A "plant promoter" is a promoter capable of initiating transcription in plant cells. Examples of promoters under developmental control include promoters that preferentially initiate transcription in certain tissues, such as leaves, roots, seeds, fibers, xylem vessels, tracheids, or sclerenchyma. Such promoters are referred to as "tissue-preferred." Promoters which initiate transcription only in certain tissue are referred to as "tissue-specific." A "cell type" specific promoter primarily drives expression in certain cell types in one or more organs, for example, vascular cells in roots or leaves. An "inducible" promoter is a promoter which is under environmental control. Examples of environmental conditions that may effect transcription by inducible promoters include anaerobic conditions or the presence of light. Tissue-specific, tissue-preferred, cell type specific, and inducible promoters constitute the class of "non-constitutive" promoters. A "constitutive" promoter is a promoter which is active under most environmental conditions.

A. Inducible Promoters:

An inducible promoter is operably linked to a gene for expression in lettuce. Optionally, the inducible promoter is operably linked to a nucleotide sequence encoding a signal sequence which is operably linked to a gene for expression in lettuce. With an inducible promoter, the rate of transcription increases in response to an inducing agent.

Any inducible promoter can be used in the instant invention. See Ward, et al., *Plant Mol. Biol.*, 22:361-366 (1993). Exemplary inducible promoters include, but are not limited to, that from the ACEI system which responds to copper (Meft, et al., *PNAS*, 90:4567-4571 (1993)); In2 gene from maize which responds to benzenesulfonamide herbicide safeners (Hershey, et al., *Mol. Gen. Genet.*, 227:229-237 (1991) and Gatz, et al., *Mol. Gen. Genet.*, 243:32-38 (1994)) or Tet repressor from Tn10 (Gatz, et al., *Mol. Gen. Genet.*, 227:229-237 (1991)). A particularly preferred inducible promoter is a promoter that responds to an inducing agent to which plants do not normally respond. An exemplary inducible promoter is the inducible promoter from a steroid hormone gene, the transcriptional activity of which is induced by a glucocorticosteroid hormone. Schena, et al., *PNAS*, 88:0421 (1991).

B. Constitutive Promoters:

A constitutive promoter is operably linked to a gene for expression in lettuce or the constitutive promoter is operably linked to a nucleotide sequence encoding a signal sequence which is operably linked to a gene for expression in lettuce.

Many different constitutive promoters can be utilized in the instant invention. Exemplary constitutive promoters include, but are not limited to, the promoters from plant viruses such as the 35S promoter from CaMV (Odell, et al., Nature, 313:810-812 (1985)) and the promoters from such genes as rice actin (McElroy, et al., Plant Cell, 2:163-171 (1990)); ubiquitin (Christensen, et al., Plant Mol. Biol., 12:619-632 (1989) and Christensen, et al., Plant Mol. Biol., 18:675-689 (1992)); pEMU (Last, et al., Theor. Appl. Genet., 81:581-588 (1991)); MAS (Velten, et al., EMBO J., 3:2723-2730 (1984)) and maize H3 histone (Lepetit, et al., Mol. Gen. Genet., 231:276-285 (1992) and Atanassova, et al., Plant J., 2 (3):291-300 (1992)). The ALS promoter, Xba1/Ncol fragment 5' to the Brassica napus ALS3 structural gene (or a nucleotide sequence similarity to said Xba1/Ncol fragment), represents a particularly useful constitutive promoter. See PCT Application No. WO 96/30530.

C. Tissue-Specific or Tissue-Preferred Promoters:

A tissue-specific promoter is operably linked to a gene for expression in lettuce. Optionally, the tissue-specific promoter is operably linked to a nucleotide sequence encoding a signal sequence which is operably linked to a gene for expression in lettuce. Plants transformed with a gene of interest operably linked to a tissue-specific promoter produce the protein product of the transgene exclusively, or preferentially, in a specific tissue.

Any tissue-specific or tissue-preferred promoter can be utilized in the instant invention. Exemplary tissue-specific or tissue-preferred promoters include, but are not limited to, a root-preferred promoter, such as that from the phaseolin gene (Murai, et al., Science, 23:476-482 (1983) and Sengupta-Gopalan, et al., *PNAS*, 82:3320-3324 (1985)); a leaf-specific and light-induced promoter such as that from cab or rubisco (Simpson, et al., EMBO J., 4(11):2723-2729 (1985) and Timko, et al., Nature, 318:579-582 (1985)); an anther-specific promoter such as that from LAT52 (Twell, et al., Mol. Gen. Genet., 217:240-245 (1989)); a pollen-specific promoter such as that from Zm13 (Guerrero, et al., Mol. Gen. Genet., 244:161-168 (1993)) or a microspore-preferred promoter such as that from apg (Twell, et al., Sex. Plant Reprod., 6:217-224 (1993)).

Signal Sequences for Targeting Proteins to Subcellular Compartments

Transport of protein produced by transgenes to a subcellular compartment such as the chloroplast, vacuole, peroxisome, glyoxysome, cell wall, or mitochondrion, or for secretion into the apoplast, is accomplished by means of operably linking the nucleotide sequence encoding a signal sequence to the 5' and/or 3' region of a gene encoding the protein of interest. Targeting sequences at the 5' and/or 3' end of the structural gene may determine, during protein synthesis and processing, where the encoded protein is ultimately compartmentalized.

The presence of a signal sequence directs a polypeptide to either an intracellular organelle or subcellular compartment or for secretion to the apoplast. Many signal sequences are known in the art. See, for example, Becker, et al., Plant Mol. Biol., 20:49 (1992); Close, P. S., Master's Thesis, Iowa State University (1993); Knox, C., et al., "Structure and Organization of Two Divergent Alpha-Amylase Genes from Barley," Plant Mol. Biol., 9:3-17 (1987); Lerner, et al., Plant Physiol., 91:124-129 (1989); Fontes, et al., Plant Cell, 3:483-496 (1991); Matsuoka, et al., PNAS, 88:834 (1991); Gould, et al., J. Cell. Biol., 108:1657 (1989); Creissen, et al., Plant J., 2:129 (1991); Kalderon, et al., A short amino acid sequence able to specify nuclear location, Cell, 39:499-509 (1984); and Steifel, et al., Expression of a maize cell wall hydroxyproline-rich glycoprotein gene in early leaf and root vascular differentiation, Plant Cell, 2:785-793 (1990).

Foreign Protein Genes and Agronomic Genes

With transgenic plants according to the present invention, a foreign protein can be produced in commercial quantities. Thus, techniques for the selection and propagation of transformed plants, which are well understood in the art, yield a plurality of transgenic plants which are harvested in a conventional manner, and a foreign protein then can be extracted from a tissue of interest or from total biomass. Protein extraction from plant biomass can be accomplished by known methods which are discussed, for example, by Heney and Orr, Anal. Biochem., 114:92-6 (1981).

According to a preferred embodiment, the transgenic plant provided for commercial production of foreign protein is lettuce. In another preferred embodiment, the biomass of interest is seed. For the relatively small number of transgenic plants that show higher levels of expression, a genetic map can be generated, primarily via conventional RFLP, PCR, and SSR analysis, which identifies the approximate chromosomal location of the integrated DNA molecule. For exemplary methodologies in this regard, see Methods in Plant Molecular Biology and Biotechnology, Glick and Thompson Eds., 269:284, CRC Press, Boca Raton (1993). Map information concerning chromosomal location is useful for proprietary protection of a subject transgenic plant. If unauthorized propagation is undertaken and crosses made with other germplasm, the map of the integration region can be compared to similar maps for suspect plants, to determine if the latter have a common parentage with the subject plant. Map comparisons would involve hybridizations, RFLP, PCR, SSR, and sequencing, all of which are conventional techniques.

Likewise, by means of the present invention, agronomic genes can be expressed in transformed plants. More particularly, plants can be genetically engineered to express various phenotypes of agronomic interest. Exemplary genes implicated in this regard include, but are not limited to, those categorized below:

A. Genes That Confer Resistance to Pests or Disease and That Encode:

1. Plant disease resistance genes. Plant defenses are often activated by specific interaction between the product of a disease resistance gene (R) in the plant and the product of a corresponding avirulence (Avr) gene in the pathogen. A plant line can be transformed with a cloned resistance gene to engineer plants that are resistant to specific pathogen strains. See, for example, Jones, et al., Science, 266:789 (1994) (cloning of the tomato Cf-9 gene for resistance to Cladosporium fulvum); Martin, et al., Science, 262:1432 (1993) (tomato Pto gene for resistance to Pseudomonas syringae pv. tomato encodes a protein kinase); and Mindrinos, et al., Cell, 78:1089 (1994) (Arabidopsis RSP2 gene for resistance to Pseudomonas syringae).

2. A Bacillus thuringiensis protein, a derivative thereof, or a synthetic polypeptide modeled thereon. See, for example, Geiser, et al., Gene, 48:109 (1986), who disclose the cloning and nucleotide sequence of a Bt δ-endotoxin gene. Moreover, DNA molecules encoding δ-endotoxin genes can be purchased from American Type Culture Collection, Manassas, Va., for example, under ATCC Accession Nos. 40098, 67136, 31995, and 31998.

3. A lectin. See, for example, the disclosure by Van Damme, et al., Plant Mol. Biol., 24:25 (1994), who disclose the nucleotide sequences of several Clivia miniata mannose-binding lectin genes.

4. A vitamin-binding protein such as avidin. See PCT Application No. US 93/06487, the contents of which are hereby incorporated by reference. The application teaches the use of avidin and avidin homologues as larvicides against insect pests.

5. An enzyme inhibitor, for example, a protease or proteinase inhibitor, or an amylase inhibitor. See, for example, Abe, et al., J. Biol. Chem., 262:16793 (1987) (nucleotide sequence of rice cysteine proteinase inhibitor); Huub, et al., Plant Mol. Biol., 21:985 (1993) (nucleotide sequence of cDNA encoding tobacco proteinase inhibitor I); and Sumitani, et al., Biosci. Biotech. Biochem., 57:1243 (1993) (nucleotide sequence of Streptomyces nitrosporeus α-amylase inhibitor).

6. An insect-specific hormone or pheromone, such as an ecdysteroid and juvenile hormone, a variant thereof, a mimetic based thereon, or an antagonist or agonist thereof. See, for example, the disclosure by Hammock, et al., Nature, 344:458 (1990), of baculovirus expression of cloned juvenile hormone esterase, an inactivator of juvenile hormone.

7. An insect-specific peptide or neuropeptide which, upon expression, disrupts the physiology of the affected pest. For example, see the disclosures of Regan, J. Biol. Chem., 269:9 (1994) (expression cloning yields DNA coding for insect diuretic hormone receptor) and Pratt, et al., Biochem. Biophys. Res. Comm., 163:1243 (1989) (an allostatin is identified in Diploptera puntata). See also, U.S. Pat. No. 5,266,317 to Tomalski, et al., who disclose genes encoding insect-specific, paralytic neurotoxins.

8. An insect-specific venom produced in nature, by a snake, a wasp, etc. For example, see Pang, et al., Gene, 116:165 (1992), for disclosure of heterologous expression in plants of a gene coding for a scorpion insectotoxic peptide.

9. An enzyme responsible for a hyper-accumulation of a monoterpene, a sesquiterpene, a steroid, hydroxamic acid, a phenylpropanoid derivative, or another non-protein molecule with insecticidal activity.

10. An enzyme involved in the modification, including the post-translational modification, of a biologically active molecule; for example, a glycolytic enzyme, a proteolytic enzyme, a lipolytic enzyme, a nuclease, a cyclase, a transaminase, an esterase, a hydrolase, a phosphatase, a kinase, a phosphorylase, a polymerase, an elastase, a chitinase, and a glucanase, whether natural or synthetic. See PCT Application No. WO 93/02197 in the name of Scott, et al., which discloses the nucleotide sequence of a callase gene. DNA molecules which contain chitinase-encoding sequences can be obtained, for example, from the ATCC under Accession Nos. 39637 and 67152. See also, Kramer, et al., Insect Biochem. Mol. Biol., 23:691 (1993), who teach the nucleotide sequence of a cDNA encoding tobacco hornworm chitinase, and Kawalleck, et al., Plant Mol. Biol., 21:673 (1993), who provide the nucleotide sequence of the parsley ubi4-2 polyubiquitin gene.

11. A molecule that stimulates signal transduction. For example, see the disclosure by Botella, et al., Plant Mol. Biol., 24:757 (1994), of nucleotide sequences for mung bean calmodulin cDNA clones, and Griess, et al., Plant Physiol., 104:1467 (1994), who provide the nucleotide sequence of a maize calmodulin cDNA clone.

12. A hydrophobic moment peptide. See PCT Application No. WO 95/16776 (disclosure of peptide derivatives of tachyplesin which inhibit fungal plant pathogens) and PCT Application No. WO 95/18855 (teaches synthetic antimicrobial peptides that confer disease resistance), the respective contents of which are hereby incorporated by reference.

13. A membrane permease, a channel former, or a channel blocker. For example, see the disclosure of Jaynes, et al., Plant Sci., 89:43 (1993), of heterologous expression of a cecropin-β, lytic peptide analog to render transgenic tobacco plants resistant to Pseudomonas solanacearum.

14. A viral-invasive protein or a complex toxin derived therefrom. For example, the accumulation of viral coat proteins in transformed plant cells imparts resistance to viral infection and/or disease development effected by the virus from which the coat protein gene is derived, as well as by related viruses. See Beachy, et al., Ann. Rev. Phytopathol., 28:451 (1990). Coat protein-mediated resistance has been conferred upon transformed plants against alfalfa mosaic virus, cucumber mosaic virus, tobacco streak virus, potato virus X, potato virus Y, tobacco etch virus, tobacco rattle virus, and tobacco mosaic virus. Id.

15. An insect-specific antibody or an immunotoxin derived therefrom. Thus, an antibody targeted to a critical metabolic function in the insect gut would inactivate an affected enzyme, killing the insect. See Taylor, et al., Abstract #497, Seventh Int'l Symposium on Molecular Plant-Microbe Interactions, Edinburgh, Scotland (1994) (enzymatic inactivation in transgenic tobacco via production of single-chain antibody fragments).

16. A virus-specific antibody. See, for example, Tavladoraki, et al., Nature, 366:469 (1993), who show that transgenic plants expressing recombinant antibody genes are protected from virus attack.

17. A developmental-arrestive protein produced in nature by a pathogen or a parasite. Thus, fungal endo-α-1, 4-D-polygalacturonases facilitate fungal colonization and plant nutrient released by solubilizing plant cell wall homo-α-1, 4-D-galacturonase. See Lamb, et al., Bio/technology, 10:1436 (1992). The cloning and characterization of a gene which encodes a bean endopolygalacturonase-inhibiting protein is described by Toubart, et al., Plant J., 2:367 (1992).

18. A developmental-arrestive protein produced in nature by a plant. For example, Logemann, et al., Bio/technology, 10:305 (1992), have shown that transgenic plants expressing the barley ribosome-inactivating gene have an increased resistance to fungal disease.

19. A lettuce mosaic potyvirus (LMV) coat protein gene introduced into *Lactuca sativa* in order to increase its resistance to LMV infection. See Dinant, et al., *Mol. Breeding*, 3:1, 75-86 (1997).

Any of the above listed disease or pest resistance genes (1-19) can be introduced into the claimed lettuce cultivar through a variety of means including but not limited to transformation and crossing.

B. Genes That Confer Resistance to an Herbicide:

1. An herbicide that inhibits the growing point or meristem, such as an imidazolinone or a sulfonylurea. Exemplary genes in this category code for mutant ALS and AHAS enzyme as described, for example, by Lee, et al., *EMBO J.*, 7:1241 (1988) and Miki, et al., *Theor. Appl. Genet.*, 80:449 (1990), respectively.

2. Glyphosate (resistance conferred by mutant 5-enolpyruvlshikimate-3-phosphate synthase (EPSPS) and aroA genes, respectively) and other phosphono compounds, such as glufosinate (phosphinothricin acetyl transferase (PAT), dicamba and *Streptomyces hygroscopicus* phosphinothricin-acetyl transferase PAT bar genes), and pyridinoxy or phenoxy proprionic acids and cyclohexones (ACCase inhibitor-encoding genes). See, for example, U.S. Pat. No. 4,940,835 to Shah, et al., which discloses the nucleotide sequence of a form of EPSPS which can confer glyphosate resistance. A DNA molecule encoding a mutant aroA gene can be obtained under ATCC Accession No. 39256, and the nucleotide sequence of the mutant gene is disclosed in U.S. Patent No. 4,769,061 to Comai. See also, Umaballava-Mobapathie in *Transgenic Research*, 8:1, 33-44 (1999) that discloses *Lactuca sativa* resistant to glufosinate. European Patent Application No. 0 333 033 to Kumada, et al., and U.S. Pat. No. 4,975,374 to Goodman, et al., disclose nucleotide sequences of glutamine synthetase genes which confer resistance to herbicides, such as L-phosphinothricin. The nucleotide sequence of a phosphinothricin-acetyl-transferase gene is provided in European Application No. 0 242 246 to Leemans, et al. DeGreef, et al., *Bio/technology*, 7:61 (1989), describe the production of transgenic plants that express chimeric bar genes coding for phosphinothricin acetyl transferase activity. Exemplary of genes conferring resistance to phenoxy proprionic acids and cyclohexones, such as sethoxydim and haloxyfop, are the Acc1-S1, Acc1-S2, and Acc1-S3 genes described by Marshall, et al., *Theor. Appl. Genet.*, 83:435 (1992).

3. An herbicide that inhibits photosynthesis, such as a triazine (psbA and gs+ genes) and a benzonitrile (nitrilase gene). Przibilla, et al., *Plant Cell*, 3:169 (1991), describe the transformation of *Chlamydomonas* with plasmids encoding mutant psbA genes. Nucleotide sequences for nitrilase genes are disclosed in U.S. Pat. No. 4,810,648 to Stalker, and DNA molecules containing these genes are available under ATCC Accession Nos. 53435, 67441, and 67442. Cloning and expression of DNA coding for a glutathione S-transferase is described by Hayes, et al., *Biochem. J.*, 285:173 (1992).

4. Acetohydroxy acid synthase, which has been found to make plants that express this enzyme resistant to multiple types of herbicides, has been introduced into a variety of plants. See Hattori, et al., *Mol. Gen. Genet.*, 246:419 (1995). Other genes that confer tolerance to herbicides include a gene encoding a chimeric protein of rat cytochrome P4507A1 and yeast NADPH-cytochrome P450 oxidoreductase (Shiota, et al., *Plant Physiol.*, 106:17 (1994)), genes for glutathione reductase and superoxide dismutase (Aono, et al., *Plant Cell Physiol.*, 36:1687 (1995)), and genes for various phosphotransferases (Datta, et al., *Plant Mol. Biol.*, 20:619 (1992)).

5. Protoporphyrinogen oxidase (protox) is necessary for the production of chlorophyll, which is necessary for all plant survival. The protox enzyme serves as the target for a variety of herbicidal compounds. These herbicides also inhibit growth of all the different species of plants present, causing their total destruction. The development of plants containing altered protox activity which are resistant to these herbicides are described in U.S. Pat. Nos. 6,288, 306, 6,282,837, 5,767,373, and International Publication WO 01/12825.

Any of the above listed herbicide genes (1-5) can be introduced into the claimed lettuce cultivar through a variety of means including, but not limited to, transformation and crossing.

C. Genes That Confer or Contribute to a Value-Added Trait, such as:

1. Increased iron content of the lettuce, for example, by introducing into a plant a soybean ferritin gene as described in Goto, et al., *Acta Horticulturae.*, 521, 101-109 (2000).

2. Decreased nitrate content of leaves, for example, by introducing into a lettuce a gene coding for a nitrate reductase. See, for example, Curtis, et al., *Plant Cell Rep.*, 18:11, 889-896 (1999).

3. Increased sweetness of the lettuce by introducing a gene coding for monellin that elicits a flavor 100,000 times sweeter than sugar on a molar basis. See Penarrubia, et al., *Bio/technology*, 10:561-564 (1992).

4. Modified fatty acid metabolism, for example, by introducing into a plant an antisense gene of stearyl-ACP desaturase to increase stearic acid content of the plant. See Knultzon, et al., *PNAS*, 89:2625 (1992).

5. Modified carbohydrate composition effected, for example, by introducing into plants a gene coding for an enzyme that alters the branching pattern of starch. See Shiroza, et al., *J. Bacteriol.*, 170:810 (1988) (nucleotide sequence of Streptococcus mutants fructosyltransferase gene); Steinmetz, et al., *Mol. Gen. Genet.*, 20:220 (1985) (nucleotide sequence of *Bacillus subtilis* levansucrase gene); Pen, et al., *Bio/technology*, 10:292 (1992) (production of transgenic plants that express *Bacillus lichenifonnis* α-amylase); Elliot, et al., *Plant Mol. Biol.*, 21:515 (1993) (nucleotide sequences of tomato invertase genes); Søgaard, et al., *J. Biol. Chem.*, 268:22480 (1993) (site-directed mutagenesis of barley α-amylase gene); and Fisher, et al., *Plant Physiol.*, 102:1045 (1993) (maize endosperm starch branching enzyme II).

D. Genes that Control Male-Sterility:

1. Introduction of a deacetylase gene under the control of a tapetum-specific promoter and with the application of the chemical N-Ac-PPT. See International Publication WO 01/29237.

2. Introduction of various stamen-specific promoters. See International Publications WO 92/13956 and WO 92/13957.

3. Introduction of the barnase and the barstar genes. See Paul, et al., *Plant Mol. Biol.*, 19:611-622 (1992).

Methods for Lettuce Transformation

Numerous methods for plant transformation have been developed, including biological and physical, plant transformation protocols. See, for example, Miki, et al., "Procedures for Introducing Foreign DNA into Plants" in *Methods in Plant Molecular Biology and Biotechnology*, Glick and Thompson Eds., CRC Press, Inc., Boca Raton, pp. 67-88 (1993). In addition, expression vectors and in vitro culture methods for plant cell or tissue transformation and regeneration of plants are available. See, for example, Gruber, et al., "Vectors for Plant Transformation" in *Methods in Plant Molecular Biology and Biotechnology*, Glick and Thompson Eds., CRC Press, Inc., Boca Raton, pp. 89-119 (1993).

A. Agrobacterium-mediated Transformation:

One method for introducing an expression vector into plants is based on the natural transformation system of *Agrobacterium*. See, for example, Horsch, et al., *Science*, 227:1229 (1985); Curtis, et al., *Journal of Experimental Botany*, 45:279, 1441-1449 (1994); Tones, et al., *Plant Cell Tissue and Organ Culture*, 34:3, 279-285 (1993); and Dinant, et al., *Molecular Breeding*, 3:1, 75-86 (1997). *A. tumefaciens* and *A. rhizogenes* are plant pathogenic soil bacteria which genetically transform plant cells. The Ti and Ri plasmids of *A. tumefaciens* and *A. rhizogenes*, respectively, carry genes responsible for genetic transformation of the plant. See, for example, Kado, C. I., *Crit. Rev. Plant Sci.*, 10:1 (1991). Descriptions of Agrobacterium vector systems and methods for Agrobacterium-mediated gene transfer are provided by Gruber, et al., supra, Miki, et al., supra, and Moloney, et al., *Plant Cell Rep.*, 8:238 (1989). See also, U.S. Pat. No. 5,591,616 issued Jan. 7, 1997.

B. Direct Gene Transfer:

Several methods of plant transformation collectively referred to as direct gene transfer have been developed as an alternative to *Agrobacterium*-mediated transformation. A generally applicable method of plant transformation is microprojectile-mediated transformation wherein DNA is carried on the surface of microprojectiles measuring 1 µm to 4 µm. The expression vector is introduced into plant tissues with a biolistic device that accelerates the microprojectiles to speeds of 300 m/s to 600 m/s which is sufficient to penetrate plant cell walls and membranes. Russell, D. R., et al., *Plant Cell Rep.*, 12 (3, January), 165-169 (1993); Aragao, F. J. L., et al., *Plant Mol. Biol.*, 20 (2, October), 357-359 (1992); Aragao, F. J. L., et al., *Plant Cell Rep.*, 12 (9, July), 483-490 (1993); Aragao, *Theor. Appl. Genet.*, 93:142-150 (1996); Kim, J., Minamikawa, T., *Plant Sci.*, 117:131-138 (1996); Sanford, et al., *Part. Sci. Technol.*, 5:27 (1987); Sanford, J. C., *Trends Biotech.*, 6:299 (1988); Klein, et al., *Bio/technology*, 6:559-563 (1988); Sanford, J. C., *Physiol. Plant*, 7:206 (1990); Klein, et al., *Bio/technology*, 10:268 (1992).

Another method for physical delivery of DNA to plants is sonication of target cells. Zhang, et al., *Bio/technology*, 9:996 (1991). Alternatively, liposome and spheroplast fusion have been used to introduce expression vectors into plants. Deshayes, et al., *EMBO J.*, 4:2731 (1985) and Christou, et al., PNAS, 84:3962 (1987). Direct uptake of DNA into protoplasts using $CaCl_2$ precipitation, polyvinyl alcohol, or poly-L-ornithine has also been reported. Hain, et al., *Mol. Gen. Genet.*, 199:161 (1985) and Draper, et al., *Plant Cell Physiol.*, 23:451 (1982). Electroporation of protoplasts and whole cells and tissues have also been described. Saker, M., Kuhne, T., *Biologia Plantarum*, 40(4):507-514 (1997/98); Donn, et al., In Abstracts of VIIth International Congress on Plant Cell and Tissue Culture IAPTC, A2-38, p. 53 (1990); D'Halluin, et al., *Plant Cell*, 4:1495-1505 (1992); and Spencer, et al., *Plant Mol. Biol.*, 24:51-61 (1994). See also Chupean, et al., *Bio/technology*, 7:5, 503-508 (1989).

Additional methods include, but are not limited to, expression vectors introduced into plant tissues using a direct gene transfer method, such as microprojectile-mediated delivery, DNA injection, electroporation, and the like. More preferably, expression vectors are introduced into plant tissues by using either microprojectile-mediated delivery with a biolistic device or by using *Agrobacterium*-mediated transformation. Transformed plants obtained with the protoplasm of the invention are intended to be within the scope of this invention.

Following transformation of lettuce target tissues, expression of the above-described selectable marker genes allows for preferential selection of transformed cells, tissues and/or plants, using regeneration and selection methods now well known in the art.

The foregoing methods for transformation would typically be used for producing a transgenic line. The transgenic line could then be crossed with another (non-transformed or transformed) line in order to produce a new transgenic lettuce line. Alternatively, a genetic trait which has been engineered into a particular lettuce cultivar using the foregoing transformation techniques could be introduced into another line using traditional backcrossing techniques that are well known in the plant breeding arts. For example, a backcrossing approach could be used to move an engineered trait from a public, non-elite inbred line into an elite inbred line, or from an inbred line containing a foreign gene in its genome into an inbred line or lines which do not contain that gene. As used herein, "crossing" can refer to a simple X by Y cross, or the process of backcrossing, depending on the context.

Gene Conversions

When the term "lettuce plant" is used in the context of the present invention, this also includes any gene conversions of that variety. The term "gene converted plant" as used herein refers to those lettuce plants which are developed by backcrossing, genetic engineering, or mutation, wherein essentially all of the desired morphological and physiological characteristics of a variety are recovered in addition to the one or more genes transferred into the variety via the backcrossing technique, genetic engineering, or mutation. Backcrossing methods can be used with the present invention to improve or introduce a characteristic into the variety. The term "backcrossing" as used herein refers to the repeated crossing of a hybrid progeny back to the recurrent parent, i.e., backcrossing 1, 2, 3, 4, 5, 6, 7, 8, 9, or more times to the recurrent parent. The parental lettuce plant which contributes the gene for the desired characteristic is termed the "nonrecurrent" or "donor parent." This terminology refers to the fact that the nonrecurrent parent is used one time in the backcross protocol and therefore does not recur. The parental lettuce plant to which the gene or genes from the nonrecurrent parent are transferred is known as the recurrent parent as it is used for several rounds in the backcrossing protocol. Poehlman & Sleper (1994) and Fehr (1993). In a typical backcross protocol, the original variety of interest (recurrent parent) is crossed to a second variety (nonrecurrent parent) that carries the gene of interest to be transferred. The resulting progeny from this cross are then crossed again to the recurrent parent and the process is repeated until a lettuce plant is obtained wherein essentially all of the desired morphological and physiological characteristics of the recurrent parent are recovered in the converted plant, in addition to the transferred gene from the nonrecurrent parent.

The selection of a suitable recurrent parent is an important step for a successful backcrossing procedure. The goal of a backcross protocol is to alter or substitute a trait or characteristic in the original line. To accomplish this, a gene of the recurrent cultivar is modified or substituted with the desired gene from the nonrecurrent parent, while retaining essentially all of the rest of the desired genetic, and therefore the desired physiological and morphological, constitution of the original line. The choice of the particular nonrecurrent parent will depend on the purpose of the backcross. One of the major purposes is to add some commercially desirable, agronomically important trait to the plant. The exact backcrossing protocol will depend on the characteristic or trait being altered to determine an appropriate testing protocol. Although backcrossing methods are simplified when the characteristic being transferred is a dominant allele, a recessive allele may also be transferred. In this instance it may be necessary to introduce a test of the progeny to determine if the desired characteristic has been successfully transferred.

Many gene traits have been identified that are not regularly selected in the development of a new line but that can be improved by backcrossing techniques. Gene traits may or may not be transgenic. Examples of these traits include, but are not limited to, male sterility, modified fatty acid metabolism, modified carbohydrate metabolism, herbicide resistance, resistance for bacterial, fungal, or viral disease, insect resistance, enhanced nutritional quality, industrial usage, yield stability, and yield enhancement. These genes are generally inherited through the nucleus. Several of these gene traits are described in U.S. Pat. Nos. 5,777,196, 5,948,957, and 5,969,212, the disclosures of which are specifically hereby incorporated by reference.

Tissue Culture

Further reproduction of the variety can occur by tissue culture and regeneration. Tissue culture of various tissues of lettuce and regeneration of plants therefrom is well known and widely published. For example, reference may be had to Teng, et al., *HortScience,* 27:9, 1030-1032 (1992); Teng, et al., HortScience, 28:6, 669-1671 (1993); Zhang, et al., *Journal of Genetics and Breeding,* 46:3, 287-290 (1992); Webb, et al., *Plant Cell Tissue and Organ Culture,* 38:1, 77-79 (1994); Curtis, et al., *Journal of Experimental Botany,* 45:279, 1441-1449 (1994); Nagata, et al., *Journal for the American Society for Horticultural Science,* 125:6, 669-672 (2000); and Ibrahim, et al., *Plant Cell Tissue and Organ Culture,* 28(2), 139-145 (1992). It is clear from the literature that the state of the art is such that these methods of obtaining plants are routinely used and have a very high rate of success. Thus, another aspect of this invention is to provide cells which upon growth and differentiation produce lettuce plants having the physiological and morphological characteristics of variety Monterra.

As used herein, the term "tissue culture" indicates a composition comprising isolated cells of the same or a different type or a collection of such cells organized into parts of a plant. Exemplary types of tissue cultures are protoplasts, calli, meristematic cells, and plant cells that can generate tissue culture that are intact in plants or parts of plants, such as leaves, pollen, embryos, roots, root tips, anthers, pistils, flowers, seeds, petioles, suckers, and the like. Means for preparing and maintaining plant tissue culture are well known in the art. By way of example, a tissue culture comprising organs has been used to produce regenerated plants. U.S. Pat. Nos. 5,959,185, 5,973,234, and 5,977,445 describe certain techniques, the disclosures of which are incorporated herein by reference.

Additional Breeding Methods

This invention also is directed to methods for producing a lettuce plant by crossing a first parent lettuce plant with a second parent lettuce plant wherein the first or second parent lettuce plant is a lettuce plant of cultivar Monterra. Further, both first and second parent lettuce plants can come from lettuce cultivar Monterra. Thus, any such methods using lettuce cultivar Monterra are part of this invention: selfing, backcrosses, hybrid production, crosses to populations, and the like. All plants produced using lettuce cultivar Monterra as at least one parent are within the scope of this invention, including those developed from cultivars derived from lettuce cultivar Monterra. Advantageously, this lettuce cultivar could be used in crosses with other, different, lettuce plants to produce the first generation ($F_1$) lettuce hybrid seeds and plants with superior characteristics. The cultivar of the invention can also be used for transformation where exogenous genes are introduced and expressed by the cultivar of the invention. Genetic variants created either through traditional breeding methods using lettuce cultivar Monterra or through transformation of cultivar Monterra by any of a number of protocols known to those of skill in the art are intended to be within the scope of this invention.

The following describes breeding methods that may be used with lettuce cultivar Monterra in the development of further lettuce plants. One such embodiment is a method for developing cultivar Monterra progeny lettuce plants in a lettuce plant breeding program comprising: obtaining the lettuce plant, or a part thereof, of cultivar Monterra, utilizing said plant or plant part as a source of breeding material, and selecting a lettuce cultivar Monterra progeny plant with molecular markers in common with cultivar Monterra and/or with morphological and/or physiological characteristics selected from the characteristics listed in Table 1. Breeding steps that may be used in the lettuce plant breeding program include pedigree breeding, backcrossing, mutation breeding, and recurrent selection. In conjunction with these steps, techniques such as RFLP-enhanced selection, genetic marker enhanced selection (for example, SSR markers), and the making of double haploids may be utilized.

Another method involves producing a population of lettuce cultivar Monterra progeny lettuce plants, comprising crossing cultivar Monterra with another lettuce plant, thereby producing a population of lettuce plants, which, on average, derive 50% of their alleles from lettuce cultivar Monterra. A plant of this population may be selected and repeatedly selfed or sibbed with a lettuce cultivar resulting from these successive filial generations. One embodiment of this invention is the lettuce cultivar produced by this method and that has obtained at least 50% of its alleles from lettuce cultivar Monterra.

One of ordinary skill in the art of plant breeding would know how to evaluate the traits of two plant varieties to determine if there is no significant difference between the two traits expressed by those varieties. For example, see Fehr and Walt, *Principles of Cultivar Development,* pp. 261-286 (1987). Thus the invention includes lettuce cultivar Monterra progeny lettuce plants comprising a combination of at least two cultivar Monterra traits selected from the group consisting of those listed in Table 1, so that said progeny lettuce plant is not significantly different for said traits than lettuce cultivar Monterra as determined at the 5% significance level when grown in the same environmental conditions. Using techniques described herein, molecular markers may be used to identify said progeny plant as a lettuce cultivar Monterra progeny plant. Mean trait values may be used to determine whether trait differences are significant, and preferably the traits are measured on plants grown under the same environmental conditions. Once such a variety is developed, its value is substantial since it is important to advance the germplasm base as a whole in order to maintain or improve traits such as yield, disease resistance, pest resistance, and plant performance in extreme environmental conditions.

Progeny of lettuce cultivar Monterra may also be characterized through their filial relationship with lettuce cultivar Monterra, as for example, being within a certain number of breeding crosses of lettuce cultivar Monterra. A breeding cross is a cross made to introduce new genetics into the progeny, and is distinguished from a cross, such as a self or a sib cross, made to select among existing genetic alleles. The lower the number of breeding crosses in the pedigree, the closer the relationship between lettuce cultivar Monterra and its progeny. For example, progeny produced by the methods described herein may be within 1, 2, 3, 4, or 5 breeding crosses of lettuce cultivar Monterra.

Tables

Tables 2-4 below compare some of the characteristics of green leaf lettuce cultivar Monterra with similar green leaf lettuce cultivar, Cielo Verde (U.S. Publication US20140259205) from a trial harvested on Jun. 30, 2013 in Soledad, Calif. Table 2 shows data for weight in pounds (lb), Table 3 shows core length in inches (in) and Table 4 shows height in inches (in). Tables 2-4, column 1 lists the data variables, column 2 shows the data for Monterra and column 3 shows the data for Cielo Verde.

TABLE 2

|  | Monterra | Cielo Verde |
|---|---|---|
|  | Weight (lb) | |
| Count | 24 | 24 |
| Sum | 19.0 | 17.4 |
| Mean | 0.79 | 0.72 |
| Maximum value | 1.0 | 0.9 |
| Minimum value | 0.6 | 0.5 |
| Variance | 0.01 | 0.01 |
| Std. deviation | 0.12 | 0.09 |
| Joint variance | 0.01 | |
| Joint degree of freedom | 46 | |
| t-test parameter | 2.232 | |
| Level of significance | 0.0305 | |
| Confidence level % | 96.948 | |

TABLE 3

|  | Monterra | Cielo Verde |
|---|---|---|
|  | Core length (in) | |
| Count | 24 | 24 |
| Sum | 33.0 | 35.3 |
| Mean | 1.38 | 1.47 |
| Maximum value | 1.5 | 1.8 |
| Minimum value | 1.0 | 1.3 |
| Variance | 0.04 | 0.02 |
| Std. deviation | 0.21 | 0.13 |
| Joint variance | 0.03 | |
| Joint degree of freedom | 46 | |
| t-test parameter | 1.852 | |
| Level of significance | 0.0704 | |
| Confidence level % | 92.959 | |

TABLE 4

|  | Monterra | Cielo Verde |
|---|---|---|
|  | Height (in) | |
| Count | 24 | 24 |
| Sum | 199.00 | 207.50 |
| Mean | 8.29 | 8.65 |
| Maximum value | 9.00 | 10.00 |
| Minimum value | 7.50 | 8.00 |
| Variance | 0.22 | 0.29 |
| Std. deviation | 0.46 | 0.54 |
| Joint variance | 0.25 | |
| Joint degree of freedom | 46.00 | |

TABLE 4-continued

|  | Monterra | Cielo Verde |
|---|---|---|
|  | Height (in) | |
| t-test parameter | 2.43 | |
| Level of significance | 0.0189 | |
| Confidence level % | 98.11 | |

As shown in Tables 2-4, lettuce cultivar Monterra has higher weight, shorter core length and shorter height than lettuce cultivar Cielo Verde.

Tables 5-8 below compare some of the characteristics of green leaf lettuce cultivar Monterra with similar green leaf lettuce cultivar, Cielo Verde (U.S. Publication US20140259205) from a trial harvested in October 2013 in California. Table 5 shows data for weight in ounces (oz), Table 6 shows data for frame diameter in inches (in), Table 7 shows core length in inches (in) and Table 8 shows height in inches (in). Tables 5-8, column 1 lists the data variables, column 2 shows the data for Monterra and column 3 shows the data for Cielo Verde.

TABLE 5

|  | Monterra | Cielo Verde |
|---|---|---|
|  | Weight (oz) | |
| Count | 18 | 18 |
| Sum | 316.4 | 293.0 |
| Mean | 17.58 | 16.28 |
| Maximum value | 23.7 | 20.0 |
| Minimum value | 12.6 | 12.5 |
| Variance | 10.22 | 4.59 |
| Std. deviation | 3.20 | 2.14 |
| Joint variance | 7.41 | |
| Joint degree of freedom | 34 | |
| t-test parameter | 1.433 | |
| Level of significance | 0.1609 | |
| Confidence level % | 83.905 | |

TABLE 6

|  | Monterra | Cielo Verde |
|---|---|---|
|  | Frame diameter (in) | |
| Count | 18 | 18 |
| Sum | 265.0 | 261.0 |
| Mean | 14.72 | 14.50 |
| Maximum value | 16.0 | 15.0 |
| Minimum value | 13.0 | 14.0 |
| Variance | 1.27 | 0.24 |
| Std. deviation | 1.13 | 0.49 |
| Joint variance | 0.75 | |
| Joint degree of freedom | 34 | |
| t-test parameter | 0.768 | |
| Level of significance | 0.4477 | |
| Confidence level % | 55.229 | |

TABLE 7

|  | Monterra | Cielo Verde |
|---|---|---|
|  | Core length (in) | |
| Count | 18 | 18 |
| Sum | 32.5 | 39.3 |
| Mean | 1.81 | 2.18 |
| Maximum value | 2.0 | 2.5 |
| Minimum value | 1.5 | 2.0 |
| Variance | 0.05 | 0.06 |
| Std. deviation | 0.22 | 0.24 |
| Joint variance | 0.05 | |
| Joint degree of freedom | 34 | |

TABLE 7-continued

| | Monterra | Cielo Verde |
|---|---|---|
| | | Core length (in) |
| t-test parameter | | 4.896 |
| Level of significance | | 0.0000 |
| Confidence level % | | 99.998 |

TABLE 8

| | Monterra | Cielo Verde |
|---|---|---|
| | | Height (in) |
| Count | 18 | 18 |
| Sum | 209.00 | 231.00 |
| Mean | 11.61 | 12.83 |
| Maximum value | 12.00 | 13.50 |
| Minimum value | 11.00 | 12.00 |
| Variance | 0.25 | 0.15 |
| Std. deviation | 0.50 | 0.38 |
| Joint variance | | 0.20 |
| Joint degree of freedom | | 34.00 |
| t-test parameter | | 8.21 |
| Level of significance | | 0.0000 |
| Confidence level % | | 100.00 |

As shown in Tables 5-8, lettuce cultivar Monterra has higher weight, shorter core length and shorter height than lettuce cultivar Cielo Verde.

Tables 9-10 below compare some of the characteristics of green leaf lettuce cultivar Monterra with similar green leaf lettuce cultivar, Bergam's Green (U.S. Plant Variety Protection certificate #200500262) from a trial harvested on Nov. 13, 2015 in Yuma, Ariz. Table 9 shows data for frame diameter in inches (in) and Table 10 shows core length in inches (in). Tables 9-10, column 1 lists the data variables, column 2 shows the data for Monterra and column 3 shows the data for Bergam's Green.

TABLE 9

| | Monterra | Bergam's Green |
|---|---|---|
| | | Frame diameter (in) |
| Count | 12 | 12 |
| Sum | 198.0 | 168.0 |
| Mean | 16.50 | 14.00 |
| Maximum value | 17.0 | 14.3 |
| Minimum value | 16.0 | 13.8 |
| Variance | 0.27 | 0.02 |
| Std. deviation | 0.52 | 0.15 |
| Joint variance | | 0.15 |
| Joint degree of freedom | | 22 |
| t-test parameter | | 15.933 |
| Level of significance | | 0.00000 |
| Confidence level % | | 100.000 |

TABLE 10

| | Monterra | Bergam's Green |
|---|---|---|
| | | Core length (in) |
| Count | 12 | 12 |
| Sum | 26.5 | 21.5 |
| Mean | 2.21 | 1.79 |
| Maximum value | 2.8 | 2.3 |
| Minimum value | 1.5 | 1.5 |
| Variance | 0.19 | 0.09 |
| Std. deviation | 0.44 | 0.30 |
| Joint variance | | 0.14 |
| Joint degree of freedom | | 22 |
| t-test parameter | | 2.726 |

TABLE 10-continued

| | Monterra | Bergam's Green |
|---|---|---|
| | | Core length (in) |
| Level of significance | | 0.0123 |
| Confidence level % | | 98.767 |

As shown in Tables 9-10, lettuce cultivar Monterra has a larger frame diameter and longer core length when compared to Bergam's Green.

As used herein, the term "plant" includes plant cells, plant protoplasts, plant cell tissue cultures from which lettuce plants can be regenerated, plant calli, plant clumps, and plant cells that are intact in plants or parts of plants, such as leaves, pollen, embryos, cotyledons, hypocotyl, roots, root tips, anthers, pistils, flowers, ovules, seeds, stems, and the like.

The use of the terms "a," "an," and "the," and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. For example, if the range 10-15 is disclosed, then 11, 12, 13, and 14 are also disclosed. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Deposit Information

A deposit of the Vanguard Seed, Inc. proprietary lettuce cultivar Monterra disclosed above and recited in the appended claims has been made with the American Type Culture Collection (ATCC), 10801 University Boulevard, Manassas, Va. 20110. The date of deposit was May 20, 2015. The deposit of 2,500 seeds was taken from the same deposit maintained by Vanguard Seed, Inc. since prior to the filing date of this application. All restrictions will be irrevocably removed upon granting of a patent, and the deposit is intended to meet all of the requirements of 37 C.F.R. §§1.801-1.809. The ATCC Accession Number is PTA-122176. The deposit will be maintained in the depository for a period of thirty years, or five years after the last request, or for the enforceable life of the patent, whichever is longer, and will be replaced as necessary during that period.

While a number of exemplary aspects and embodiments have been discussed above, those of skill in the art will recognize certain modifications, permutations, additions, and sub-combinations thereof. It is therefore intended that the following appended claims and claims hereafter introduced are interpreted to include all such modifications, permutations, additions, and sub-combinations as are within their true spirit and scope.

What is claimed is:

1. A seed of lettuce cultivar Monterra, wherein a representative sample seed of said cultivar was deposited under ATCC Accession No. PTA-122176.

2. A lettuce plant, or a part thereof, produced by growing the seed of claim 1.

3. A tissue culture produced from protoplasts or cells from the plant of claim 2, wherein said cells or protoplasts are produced from a plant part selected from the group consisting of leaf, pollen, embryo, cotyledon, hypocotyl, meristematic cell root, root tip, pistil, anther, ovule, flower, shoot, stem, seed, and petiole.

4. A lettuce plant regenerated from the tissue culture of claim 3, wherein the plant has all of the morphological and physiological characteristics of cultivar Monterra.

5. A method for producing a lettuce seed, said method comprising crossing two lettuce plants and harvesting the resultant lettuce seed, wherein at least one lettuce plant is the lettuce plant of claim 2.

6. An $F_1$ lettuce seed produced by the method of claim 5.

7. An $F_1$ lettuce plant, or a part thereof, produced by growing said seed of claim 6.

8. The method of claim 5, wherein at least one of said lettuce plants is transgenic.

9. A method of producing a male sterile lettuce plant, wherein the method comprises introducing a nucleic acid molecule that confers male sterility into the lettuce plant of claim 2.

10. A male sterile lettuce plant produced by the method of claim 9, wherein said plant comprises said nucleic acid and otherwise comprises all of the physiological and morphological characteristics of lettuce cultivar Monterra as listed in Table 1.

11. A method of producing an herbicide resistant lettuce plant, wherein said method comprises introducing a gene conferring herbicide resistance into the plant of claim 2, wherein the herbicide resistance is selected from the group consisting of glyphosate, sulfonylurea, imidazolinone, dicamba, glufosinate, phenoxy proprionic acid, L-phosphinothricin, cyclohexone, cyclohexanedione, triazine, and benzonitrile.

12. An herbicide resistant lettuce plant produced by the method of claim 11, wherein said plant comprises said gene and otherwise comprises all of the physiological and morphological characteristics of lettuce cultivar Monterra as listed in Table 1.

13. A method of producing a pest or insect resistant lettuce plant, wherein said method comprises introducing a gene conferring pest or insect resistance into the plant of claim 2.

14. A pest or insect resistant lettuce plant produced by the method of claim 13, wherein said plant comprises said gene and otherwise comprises all of the physiological and morphological characteristics of lettuce cultivar Monterra as listed in Table 1.

15. The lettuce plant of claim 14, wherein the gene encodes a *Bacillus thuringiensis* endotoxin.

16. A method of producing a disease resistant lettuce plant, wherein said method comprises introducing a gene conferring disease resistance into the plant of claim 2.

17. A disease resistant lettuce plant produced by the method of claim 16, wherein said plant comprises said gene and otherwise comprises all of the physiological and morphological characteristics of lettuce cultivar Monterra as listed in Table 1.

18. A method of producing a lettuce plant with a value-added trait, wherein said method comprises introducing a gene conferring a value-added trait into the plant of claim 2, where said gene encodes a protein selected from the group consisting of a ferritin, a nitrate reductase, and a monellin.

19. A lettuce plant with a value-added trait produced by the method of claim 18, wherein said plant comprises said gene and otherwise comprises all of the physiological and morphological characteristics of lettuce cultivar Monterra as listed in Table 1.

20. A method of introducing a desired trait into lettuce cultivar Monterra wherein the method comprises:
(a) crossing a Monterra plant, wherein a representative sample of seed was deposited under ATCC Accession No. PTA-122176, with a plant of another lettuce cultivar that comprises a desired trait, wherein the desired trait is selected from the group consisting of male sterility, herbicide resistance, insect or pest resistance, modified bolting and resistance to bacterial disease, fungal disease and viral disease;
(b) selecting one or more progeny plants that have the desired trait;
(c) backcrossing the selected progeny plants with lettuce cultivar Monterra plants to produce backcross progeny plants;
(d) selecting for backcross progeny plants that have the desired trait; and
(e) repeating steps (c) and (d) two or more times in succession to produce selected third or higher backcross progeny plants that comprise the desired trait.

21. A lettuce plant produced by the method of claim 20, wherein the plant has the desired trait and otherwise all of the physiological and morphological characteristics of lettuce cultivar Monterra.

22. The lettuce plant of claim 21, wherein the desired trait is herbicide resistance and the resistance is conferred to an herbicide selected from the group consisting of glyphosate, sulfonylurea, imidazolinone, dicamba, glufosinate, phenoxy proprionic acid, L-phosphinothricin, cyclohexone, cyclohexanedione, triazine, and benzonitrile.

23. The lettuce plant of claim 21, wherein the desired trait is insect or pest resistance and the insect or pest resistance is conferred by a transgene encoding a *Bacillus thuringiensis* endotoxin.

* * * * *